US006255558B1

(12) United States Patent
Haseloff et al.

(10) Patent No.: US 6,255,558 B1
(45) Date of Patent: Jul. 3, 2001

(54) GENE EXPRESSION

(75) Inventors: James Philip Haseloff, Comberton; Sarah Hodge, Cambridge, both of (GB)

(73) Assignee: BTG International Limited, London (GB)

( * ) Notice: Subject to any disclaimer, the term of this patent is extended or adjusted under 35 U.S.C. 154(b) by 0 days.

(21) Appl. No.: 09/133,321

(22) Filed: Aug. 13, 1998

(30) Foreign Application Priority Data

Feb. 14, 1996 (GB) .................................................. 9603069
Feb. 14, 1997 (GB) .................................... PCT/GB97/00406

(51) Int. Cl.[7] ............................. C12N 5/04; C12N 15/29; C12N 15/82; C12N 15/84; A01H 5/00
(52) U.S. Cl. ..................... 800/278; 435/69.1; 435/320.1; 435/419; 435/468; 536/24.1; 800/288; 800/294; 800/298
(58) Field of Search ................................ 435/69.1, 320.1, 435/419, 468; 536/24.1; 800/278, 288, 295, 294, 298

(56) References Cited

U.S. PATENT DOCUMENTS

| 5,801,027 | * | 9/1998 | Bennet et al. ........................ 435/468 |
| 5,866,384 | | 2/1999 | Haseloff et al. ...................... 435/468 |
| 5,968,793 | | 10/1999 | Liu et al. ............................. 435/69.1 |

FOREIGN PATENT DOCUMENTS

| 0 359 472 A2 | 3/1990 | (EP) | ............................. C12N/15/82 |
| 0 385 962 A1 | 9/1990 | (EP) | ............................. C12N/15/32 |
| 0 589 841 A2 | 3/1994 | (EP) | ............................. C12N/15/82 |
| 90/01551 | 2/1990 | (WO) | ............................. C12N/15/82 |
| 95/33055 | 12/1995 | (WO) | ............................. C12N/15/53 |
| 96/27675 | 9/1996 | (WO) | ............................. C12N/15/82 |

OTHER PUBLICATIONS

Ma et al, "Yeast activators stimulate plant gene expression," Nature, vol. 334, No. 18, pp. 631–633 (1988).
Brand et al, "Targeted gene expression as a means of altering cell . . . ," Development, vol. 118, No. 2, pp. 401–415 (1993).
Greig et al, "Homeotic genes autonomously specify one aspect of . . . ," Nature, vol. 362, No. 15, pp. 630–632 (1993).
Reichel et al, "Inefficient expression of the DNA–binding domain . . . ," Plant Cell Reports, vol. 14, pp. 773–776 (1995).
Adang et al, Plant Mol. Biol., vol. 21, pp. 1131–1145, 1993.*
Rocholl et al, Plant Sci., vol. 97, pp. 189–198, 1994.*
Akama et al, Plant Cell Rep., vol. 12, pp. 7–11, 1992.*
Woontner et al, Mol. Cell. Biol., vol. 11, pp. 4555–4560, 1991.*

* cited by examiner

Primary Examiner—Gary Benzion
Assistant Examiner—Ashwin D. Mehta
(74) Attorney, Agent, or Firm—Nixon & Vanderhye

(57) ABSTRACT

Disclosed is a nucleic acid sequence, expressible in a plant cell, encoding at least an effective portion of a GAL4 DNA-binding domain, the sequence having a % A/T base content substantially reduced relative to the wild-type yeast sequence.

22 Claims, 6 Drawing Sheets

```
                                                                                          A/T
                                                                                          content
         HinD III  BamH I           32/11
                   atg aag cta ctg tct tct atc gaa caa gca tgc gat att tgc                60%
         aagctt ggatcc aaca atg aag ctc ctc tcc atc gag cag gcc tgc gac atc tgc           40%
                        M   K   L   L   S   S   I   E   Q   A   C   D   I   C
   62/21                                    92/31
         cga ctt aaa aag ctc aag tgc tcc aaa gaa acc aag tgc gcc aag tgt ctg aag aac      55%
         cgc ctc aag aag ctc aag tgc tcc aag gag aag ccg aag tgc gcc aag tgt ctg aag aac  45%
           R   L   K   K   L   K   C   S   K   E   K   P   K   C   A   K   C   L   K   N
  122/41                              152/51
         aac tgg gag tgt cgc tac tct ccc aaa acc aaa agg tct ccg ctg act agg gca cat ctg  47%
         aac tgg gag tgt cgc tac tct ccc aaa acc aag cgc tcc ccg ctg acc cgc gcc cac ctc  35%
           N   W   E   C   R   Y   S   P   K   T   K   R   S   P   L   T   R   A   H   L
  182/61                                  212/71                                 Xho I
         aca gaa gtg gaa tca agg cta gaa aga cag cta gaa cag cta ttt cta ctg att ttt cct cga  60%
         acc gaa gtg gag tcc cgc ctg gag cag cgc ctg gag cag ctc ttc ctc ctg atc ttc cct cga  37%
           T   E   V   E   S   R   L   E   R   L   E   Q   L   F   L   L   I   F   P   R
  242/81                                 272/91
         gaa gac ctt gac atg att ttg aaa atg gat tct tta cag gat ata aaa gca ttg tta aca  70%
         gag gac ctc gac atg atc ctg aaa atg gat tcc ctc cag gat atc aaa gcc ctg ctc acc  42%
           E   D   L   D   M   I   L   K   M   D   S   L   Q   D   I   K   A   L   L   T
  302/101                             332/111
         gga tta ttt gta caa gat aat gtg aat aaa gat gcc gtc aca gat aga ttg gct tca gtg  63%
         ggc ctc ttc gtc cag gac aac gtg aac aaa gac gcc gtc acc gac cgc ctg gcc tcc gtg  35%
           G   L   F   V   Q   D   N   V   N   K   D   A   V   T   D   R   L   A   S   V
```

Fig.1a.

```
362/121
gag act gat atg cct cta aca ttg aga cag cat aga ata agt gcg aca tca tca tcg gaa    58%
 E   T   D   M   P   L   T   L   R   Q   H   R   I   S   A   T   S   S   S   E
gag acc gac atg ccc ctc acc ctg cag cac cgc cag cac atc agc gcg acc tcc tcc tcg gag   30%
                              392/131
422/141
gag agt agt aac aaa ggt caa aga cag ttg act gta tcg acg gcc ccc ccg acc gat gtc    47%
 E   S   S   N   K   G   Q   R   Q   L   T   V   S   T   A   P   P   T   D   V
gag agc agc aac aag ggc cag cgc cag cac ttg acc gtc acg gcc ccc ccg acc gac gtc    30%
              Sac I                 452/151
482/161
agc ctg ggg gac gag ctc cac tta gac atg gcg gtg gag gac atg gcg cat gcc gac gcg   30%
 S   L   G   D   E   L   H   L   D   G   V   A   M   A   H   A   D   A
agc ctg ggg gac gag ctc cac tta gac atg gcg gtg gag gac atg gcg cat gcc gac gcg
              512/171
542/181
cta gac gat ttc gat ctg gat ttg ggg gac ggg gat tcc ccg ggg ccg ttc gag ttt acc    40%
 L   D   D   F   D   L   D   L   G   D   G   D   S   P   G   P   F   E   F   T
cta gac gat ttc gat ctg gat ttg ggg gac ggg gat tcc ccg gga ccg tga ttt acc
              572/191
602/201
ccc cac gac tcc ccc gcc gct ctg gat atg gcc gac ttc gag cag atg    37%
 P   H   D   S   P   A   A   L   D   M   A   D   F   E   Q   M
ccc cac gac tcc ccc gcc gct ctg gat atg gcc gac ttc gag cag atg
              632/211
662/221
ttt acc gat gcc ctt gga att gac gag tac ggt ggg tag
 F   T   D   A   L   G   I   D   E   Y   G   G   *
ttt acc gat gcc ctt gga att gac gag tac ggt ggg tagatct
              692/231            Bgl II
```

Modified Ti plasmid right border

TAGGTTTACCCGCCAATATATCCTGTCAAACACT GGATCTTCGCAAGACCCTT
    |------25 bp repeat-----| mRNA start
                                                |
CCTCTATATAAGGAAGTTCATTTCATTTGGAGAGGACA..GAL4 gene..
    TATA Box X
USA-nGUS

SEQUENCE LISTING (1) GENERAL INFORMATION:

(iii) NUMBER OF SEQUENCES: 15

(2) INFORMATION FOR SEQ ID NO: 1:

(i) SEQUENCE CHARACTERISTICS:

(A) LENGTH: 701 base pairs
        (B) TYPE: nucleic acid
        (C) STRANDEDNESS: single
        (D) TOPOLOGY: linear (ix) FEATURE:
        (A) NAME/KEY: CDS
        (B) LOCATION:17..694

(xi) SEQUENCE DESCRIPTION: SEQ ID NO: 1:

```
AAGCTTGGAT CCAACA ATG AAG CTC CTG TCC TCC ATC GAG CAG GCC TGC         49
               Met Lys Leu Leu Ser Ser Ile Glu Gln Ala Cys
                 1               5                      10

GAC ATC TGC CGC CTC AAG AAG CTC AAG TGC TCC AAG GAG AAG CCG AAG       97
Asp Ile Cys Arg Leu Lys Lys Leu Lys Cys Ser Lys Glu Lys Pro Lys
            15                  20                  25

TGC GCC AAG TGT CTG AAG AAC AAC TGG GAG TGT CGC TAC TCT CCC AAA      145
Cys Ala Lys Cys Leu Lys Asn Asn Trp Glu Cys Arg Tyr Ser Pro Lys
        30                  35                  40

ACC AAG CGC TCC CCG CTG ACC CGC GCC CAC CTC ACC GAA GTG GAG TCC      193
Thr Lys Arg Ser Pro Leu Thr Arg Ala His Leu Thr Glu Val Glu Ser
    45                  50                  55

CGC CTG GAG CGC CTG GAG CAG CTC TTC CTC CTG ATC TTC CCT CGA GAG      241
Arg Leu Glu Arg Leu Glu Gln Leu Phe Leu Leu Ile Phe Pro Arg Glu
60                  65                  70                  75

GAC CTC GAC ATG ATC CTG AAA ATG GAC TCC CTC CAG GAC ATC AAA GCC      289
Asp Leu Asp Met Ile Leu Lys Met Asp Ser Leu Gln Asp Ile Lys Ala
                80                  85                  90

CTG CTC ACC GGC CTC TTC GTC CAG GAC AAC GTG AAC AAA GAC GCC GTC      337
Leu Leu Thr Gly Leu Phe Val Gln Asp Asn Val Asn Lys Asp Ala Val
            95                 100                 105

ACC GAC CGC CTG GCC TCC GTG GAG ACC GAC ATG CCC CTC ACC CTG CGC      385
Thr Asp Arg Leu Ala Ser Val Glu Thr Asp Met Pro Leu Thr Leu Arg
        110                 115                 120

CAG CAC CGC ATC AGC GCG ACC TCC TCC TCG GAG GAG AGC AGC AAC AAG      433
Gln His Arg Ile Ser Ala Thr Ser Ser Ser Glu Glu Ser Ser Asn Lys
    125                 130                 135

GGC CAG CGC CAG TTG ACC GTC TCG ACG GCC CCC CCG ACC GAC GTC AGC      481
Gly Gln Arg Gln Leu Thr Val Ser Thr Ala Pro Pro Thr Asp Val Ser
140                 145                 150                 155

CTG GGG GAC GAG CTC CAC TTA GAC GGC GAG GAC GTG GCG ATG GCG CAT      529
Leu Gly Asp Glu Leu His Leu Asp Gly Glu Asp Val Ala Met Ala His
                160                 165                 170

GCC GAC GCG CTA GAC GAT TTC GAT CTG GAC ATG TTG GGG GAC GGG GAT      577
Ala Asp Ala Leu Asp Asp Phe Asp Leu Asp Met Leu Gly Asp Gly Asp
            175                 180                 185

TCC CCG GGG CCG GGA TTT ACC CCC CAC GAC TCC GCC CCC TAC GGC GCT      625
Ser Pro Gly Pro Gly Phe Thr Pro His Asp Ser Ala Pro Tyr Gly Ala
        190                 195                 200

CTG GAT ATG GCC GAC TTC GAG TTT GAG CAG ATG TTT ACC GAT GCC CTT      673
Leu Asp Met Ala Asp Phe Glu Phe Glu Gln Met Phe Thr Asp Ala Leu
    205                 210                 215

GGA ATT GAC GAG TAC GGT GGG TAGATCT                                  701
Gly Ile Asp Glu Tyr Gly Gly
220                 225
```

(2) INFORMATION FOR SEQ ID NO: 2:

(i) SEQUENCE CHARACTERISTICS:
        (A) LENGTH: 226 amino acids
        (B) TYPE: amino acid
        (D) TOPOLOGY: linear (ii) MOLECULE TYPE: protein (xi) SEQUENCE DESCRIPTION: SEQ ID NO: 2:

```
Met Lys Leu Leu Ser Ser Ile Glu Gln Ala Cys Asp Ile Cys Arg Leu
 1               5                  10                  15

Lys Lys Leu Lys Cys Ser Lys Glu Lys Pro Lys Cys Ala Lys Cys Leu
            20                  25                  30

Lys Asn Trp Glu Cys Arg Tyr Ser Pro Lys Thr Lys Arg Ser Pro
        35                  40                  45

Leu Thr Arg Ala His Leu Thr Glu Val Glu Ser Arg Leu Glu Arg Leu
        50                  55                  60

Glu Gln Leu Phe Leu Leu Ile Phe Pro Arg Glu Asp Leu Asp Met Ile
 65                  70                  75                  80

Leu Lys Met Asp Ser Leu Gln Asp Ile Lys Ala Leu Leu Thr Gly Leu
                85                  90                  95

Phe Val Gln Asp Asn Val Asn Lys Asp Ala Val Thr Asp Arg Leu Ala
                100                 105                 110

Ser Val Glu Thr Asp Met Pro Leu Thr Leu Arg Gln His Arg Ile Ser
            115                 120                 125

Ala Thr Ser Ser Ser Glu Glu Ser Ser Asn Lys Gly Gln Arg Gln Leu
    130                 135                 140

Thr Val Ser Thr Ala Pro Pro Thr Asp Val Ser Leu Gly Asp Glu Leu
145                 150                 155                 160

His Leu Asp Gly Glu Asp Val Ala Met Ala His Ala Asp Ala Leu Asp
                165                 170                 175

Asp Phe Asp Leu Asp Met Leu Gly Asp Gly Asp Ser Pro Gly Pro Gly
                180                 185                 190

Phe Thr Pro His Asp Ser Ala Pro Tyr Gly Ala Leu Asp Met Ala Asp
            195                 200                 205

Phe Glu Phe Glu Gln Met Phe Thr Asp Ala Leu Gly Ile Asp Glu Tyr
    210                 215                 220

Gly Gly
225
```

(2) INFORMATION FOR SEQ ID NO: 3:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (xi) SEQUENCE DESCRIPTION: SEQ ID NO: 3:

GGCAACAATG AAGCTACTGT CTTCTATC                                      28

(2) INFORMATION FOR SEQ ID NO: 4:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (xi) SEQUENCE DESCRIPTION: SEQ ID NO: 4:

GGCAGATCTA CCCACCGTAC TCGTCAATTC C                                  31

(2) INFORMATION FOR SEQ ID NO: 5:

(i) SEQUENCE CHARACTERISTICS:

(A) LENGTH: 109 base pairs
        (B) TYPE: nucleic acid
        (C) STRANDEDNESS: single
        (D) TOPOLOGY: linear (xi) SEQUENCE DESCRIPTION: SEQ ID NO: 5:

GGCAAGCTTG GATCCAACAA TGAAGCTCCT GTCCTCCATC GAGCAGGCCT GCGACATCTG       60

CCGCCTCAAG AAGCTCAAGT GCTCCAAGGA GAAGCCGAAG TGCGCCAAG                  109

(2) INFORMATION FOR SEQ ID NO: 6:

(i) SEQUENCE CHARACTERISTICS:
        (A) LENGTH: 108 base pairs
        (B) TYPE: nucleic acid
        (C) STRANDEDNESS: single
        (D) TOPOLOGY: linear (xi) SEQUENCE DESCRIPTION: SEQ ID NO: 6:

TCCTCTCGAG GGAAGATCAG GAGGAAGAGC TGCTCCAGGC GCTCCAGGCG GGACTCCACT       60

TCGGTGAGGT GGGCGCGGGT CAGCGGGGAG CGCTTGGTTT TGGGAGAG                   108

(2) INFORMATION FOR SEQ ID NO: 7:

(i) SEQUENCE CHARACTERISTICS:
        (A) LENGTH: 81 base pairs
        (B) TYPE: nucleic acid
        (C) STRANDEDNESS: single
        (D) TOPOLOGY: linear (xi) SEQUENCE DESCRIPTION: SEQ ID NO: 7:

TTCCCTCGAG AGGACCTCGA CATGATCCTG AAAATGGACT CCCTCCAGGA CATCAAAGCC       60

CTGCTCACCG GCCTCTTCGT C                                                81

(2) INFORMATION FOR SEQ ID NO: 8:

(i) SEQUENCE CHARACTERISTICS:
        (A) LENGTH: 89 base pairs
        (B) TYPE: nucleic acid
        (C) STRANDEDNESS: single
        (D) TOPOLOGY: linear (xi) SEQUENCE DESCRIPTION: SEQ ID NO: 8:

GGGTGAGGGG CATGTCGGTC TCCACGGAGG CCAGGCGGTC GGTGACGGCG TCTTTGTTCA       60

CGTTGTCCTG GACGAAGAGG CCGGTGAGC                                        89

(2) INFORMATION FOR SEQ ID NO: 9:

(i) SEQUENCE CHARACTERISTICS:
        (A) LENGTH: 80 base pairs
        (B) TYPE: nucleic acid
        (C) STRANDEDNESS: single
        (D) TOPOLOGY: linear (xi) SEQUENCE DESCRIPTION: SEQ ID NO: 9:

GGAGACCGAC ATGCCCCTCA CCCTGCGCCA GCACCGCATC AGCGCGACCT CCTCCTCGGA       60

GGAGAGCAGC AACAAGGGCC                                                  80

(2) INFORMATION FOR SEQ ID NO: 10:

(i) SEQUENCE CHARACTERISTICS:
        (A) LENGTH: 83 base pairs
        (B) TYPE: nucleic acid
        (C) STRANDEDNESS: single
        (D) TOPOLOGY: linear (xi) SEQUENCE DESCRIPTION: SEQ ID NO: 10:

```
AGTGGAGCTC GTCCCCCAGG CTGACGTCGG TCGGGGGGGC CGTCGAGACG GTCAACTGGC    60

GCTGGCCCTT GTTGCTGCTC TCC                                           83
```

(2) INFORMATION FOR SEQ ID NO: 11:

(i) SEQUENCE CHARACTERISTICS:
        (A) LENGTH: 56 base pairs
        (B) TYPE: nucleic acid
        (C) STRANDEDNESS: single
        (D) TOPOLOGY: linear (xi) SEQUENCE DESCRIPTION: SEQ ID NO: 11:

```
ATATCCTGTC AAACACTGGA TCCGAGCTCC AATTCATAGT TTAAACTGAA GGCGGG        56
```

(2) INFORMATION FOR SEQ ID NO: 12:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (xi) SEQUENCE DESCRIPTION: SEQ ID NO: 12:

```
GGCAGATCTT CGCAAGACCC TTCCTCTATA TAAGG                               35
```

(2) INFORMATION FOR SEQ ID NO: 13:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO: 13:

```
CACACAAACG GTGATACGTA                                                20
```

(2) INFORMATION FOR SEQ ID NO: 14:

(i) SEQUENCE CHARACTERISTICS:
        (A) LENGTH: 59 base pairs
        (B) TYPE: nucleic acid
        (C) STRANDEDNESS: single
        (D) TOPOLOGY: linear (xi) SEQUENCE DESCRIPTION: SEQ ID NO: 14:

```
GAACTCTAGA AGCTACTCCA CGTCCATAAG GGACACATCA CAATCCCACT ATCCTTCGC     59
```

(2) INFORMATION FOR SEQ ID NO: 15:

(i) SEQUENCE CHARACTERISTICS:
        (A) LENGTH: 91 base pairs
        (B) TYPE: nucleic acid
        (C) STRANDEDNESS: single
        (D) TOPOLOGY: linear (xi) SEQUENCE DESCRIPTION: SEQ ID NO: 15:

```
TAGGTTTACC CGCCAATATA TCCTGTCAAA CACTGGATCT TCGCAAGACC CTTCCTCTAT    60

ATAAGGAAGT TCATTTCATT TGGAGAGGAC A                                   91
```

GENE EXPRESSION

FIELD OF THE INVENTION

This invention relates to a nucleic acid sequence optimised for expression in a plant cell, and to vectors and plant cells comprising the nucleic acid sequence.

BACKGROUND OF THE INVENTION

In yeast there is a gene called GAL4, the product of which acts as a transcriptional activator (Johnston 1987 Microbiol. Rev. 51, 458–476). The GAL4 gene is quite large (3 Kb) and the encoded polypeptide comprises an N-terminal DNA-binding domain, a C terminal domain having a transcriptional activator function, and an intervening glucose-responsive element "GRE" (GAL4 being repressed in the presence of glucose).

The GAL4 protein has been quite well characterised. Amino acid residues 1–147 of the protein bind to DNA in a sequence-specific manner (Keegan et al 1986 Science 231, 699–704). The transcriptional activation function is associated with two short portions of the C terminal domain (Ma & Ptashne 1987 Cell 48, 847–853). The DNA sequence to which GAL4 binds has been identified as a 17 mer, which must be present as a repeat for optimal GAL4 binding (Giniger et al, 1985 Cell 40, 767–774), and may be referred to as a GAL4-responsive "upstream activation sequence" (UAS): GAL4 binds to the UAS 5' of a gene by means of the DNA-binding domain, and the C-terminal domain causes up-regulation of transcription of the gene.

Recently, a two-element system has been developed for directing gene expression in *Drosophila melanogaster*. Brand and Perrimon (1993 Development 118: 401–415,) randomly inserted the gene encoding the GAL4 into the Drosophila genome using a P-element based vector.

A large number of stable Drosophila lines were generated which each express GAL4 in a particular pattern, dependent on adjacent genomic DNA sequences. A chosen target gene could then be cloned under the control of GAL4 upstream activation sequences (UAS); separately transformed, and maintained silently in the absence of GAL4. Genetic crossing of this single line with any of the library of GAL4-containing lines allowed activation of the target gene in many different tissue and cell types, and the phenotypic consequences of mis-expression, including those lethal to the organism, could be conveniently studied. In addition, the library of GAL4-containing flies has become an increasingly characterised and shared resource, and which provides a common entry point for various "reverse" genetic techniques.

A similar system operable in plants would be highly desirable. However, expression of heterologous eukaryotic genes in plants has proved highly problematical in the past (see, for example, Green Fluorescent Protein) and efficient expression of GAL4 appears equally difficult, and it has been suggested that this is due to inefficient translation of GAL4 mRNA in plants (Reichel et al, 1995 Plant Cell Reports 14, 773–776). Ma et al, (1988 Nature 334, 631–633) were able to obtain transient expression of modified, functional GAL4 derivatives in tobacco-leaf protoplasts but could not demonstrate the presence of functional, full-length wild-type GAL4. Similarly, transient expression of GAL4 derivatives has been demonstrated in maize protoplasts (McCarty et al, 1991 Cell 66, 895–905) and when introduced by biolistic methods, in maize aleurone tissues or embryogenic calli (Goff et al, 1991 Genes & Dev. 5, 298–309; Goff et al, 1992 Genes & Dev. 6, 864–875).

Hitherto however, there have been no reports of stable, efficient expression of functional GAL4 or derivaties thereof in a plant cell.

It is an aim of the present invention to provide a novel expression system operable in plants, utilising a modified portion of the GAL4 gene.

SUMMARY OF THE INVENTION

In a first aspect the invention provides a nucleic acid sequence, expressible in a plant cell, encoding at least an effective portion of a GAL4 DNA-binding domain, the sequence having an A/T base content substantially reduced relative to the wild-type yeast sequence.

The A/T content of the wild-type yeast sequence encoding the DNA-binding domain of GAL4 is about 59%. The % A/T base content of the sequence of the invention encoding the effective portion of the GAL4 DNA-binding domain will be understood to be substantially reduced when it is less than 50%. Preferably the A/T content is less than 45%, and more preferably less than 40%. The sequence of the invention may be made, for example, by site-directed mutagenesis, or be made de novo by chemical synthesis.

An "effective portion" of the DNA-binding domain is a portion sufficient to retain most (i.e. over 50%) of the DNA-binding activity of the full length DNA-binding domain. Typically the "effective portion" will comprise at least two thirds of the full length sequence of the DNA-binding domain. Conveniently the nucleic acid sequence will encode substantially all of the GAL4 DNA-binding domain (i.e. amino acid residues 1–147 of the yeast polypeptide), although a substantially smaller portion (about 75 amino acid residue) is quite adequate to retain most of the DNA-binding activity (Kraulis et al, 1992 Nature 356, 448–450; and Marmorstein et al, 1992 Nature 356, 408–414). In one particular embodiment, the sequence will comprise the nucleotide sequence shown in the 5' portion (nucleotides 1 to about 460) of FIG. 1, which sequence has a substantially reduced A/T content (38%), relative to the wild-type yeast sequence, yet encodes an identical amino acid sequence.

The GAL4 DNA-binding domain has no transcriptional activation function in its own right. Thus, in preferred embodiments, the sequence encoding the effective portion of the GAL4 DNA-binding domain will be operably linked to one or more other nucleic acid sequences, which sequences may be structural (i.e. encode functional polypeptides) and/or regulatory. Typically the sequence encoding the DNA-binding domain will be operably linked (e.g. fused in-frame) to a sequence encoding a peptide or polypeptide with a regulatory function, preferably a transcriptional activator. The transcriptional activator may be the activation domain of GAL4 protein, the sequence encoding which should preferably be optimised for expression in plants (e.g. by reducing the A/T content thereof). Alternatively, the transcriptional activator could be any one of a number of such proteins known to be active in plants, which will be well-known to those skilled in the art, such that the sequence of the invention encodes a chimeric polypeptide, comprising at least an effective portion of the GAL4 DNA-binding domain and a transcriptional activation domain. A particularly suitable transcriptional activator domain is that obtainable from herpes simplex virus (HSV) VP-16, (see Greaves and O'Hare 1989 J. Virol 63, 1641–1650; VP, being also known as VMW65). Other transcriptional activation domains include certain peptides encoded by *E. coli* genomic DNA fragments (Ma & Ptashne 1987 Cell 51, 113–119) or synthetic peptides designed to form amphiphilic α-helix (Giniger & Ptashne 1987 Nature 330, 670–672). A common feature appears to be the requirement for excess charge, either positive (Gill & Ptashne 1987 Cell 51, 121–126) or, more especially for plant activation domains, excess negative charge (Estruch et al, 1994 Nucl. Acids Res. 22, 3983–3989). With this in mind, the person skilled in the art could readily synthesise, or find naturally-occurring sequences, which encode peptides or polypeptides with transcriptional activation activity in plants. Such activator sequences may, in any event, be modified for optimal activity in a plant cell.

In a further aspect the invention provides a nucleic acid construct, comprising the nucleic acid sequence defined above. In one particular embodiment, the nucleic acid construct could be used as an "enhancer-trap" to "fish" for plant enhancer sequences (Cf. Sundaresan et al, 1995 Genes & Dev. 9, 1797–1810). In such an embodiment, the construct will preferably include right and left Ti-DNA, to allow for random, stable insertion into the genome of a plant cell host. The construct will preferably comprise a naive plant promoter sequence, by which term is meant a promoter (operable in a plant cell) which requires the presence of a suitable enhancer sequence to cause substantial levels of transcription. Such a "naive" promoter may be thought of as an "enhancer-dependent" promoter, and essentially corresponds to the TATA box region of known plant promoters. "Plant" promoters includes reference to viral and bacterial promoter sequences which are active in a plant cell (e.g. nucleotides –48 to +1 of the CaMV 35S promoter). The naive promoter is conveniently substantially adjacent to one Ti border, the promoter being in competent relationship with the sequence encoding the GAL4 DNA-binding domain fused with a transcription activation domain operable in plants such that, should the promoter become inserted in the plant host cell genome in functional relationship with an enhancer sequence, the promoter will direct the expression of the GAL4 DNA-binding domain and the transcriptional activation domain. The construct may additionally comprise a plant selectable marker (e.g. Kanamycin resistance) for convenience. Additionally, the construct may comprise a reporter gene active in plants (such as Green Fluorescent Protein, or β-glucuronidase "GUS") in operable linkage to a GAL4-responsive upstream activation sequence (UAS), such that the reporter gene will be expressed in response to synthesis of the GAL4 DNA-binding domain/transcriptional activator fusion protein. Preferably the reporter gene is modified GFP as disclosed in WO 96/27675, or GUS (conveniently with a nuclear localisation signal). Preferably the UAS comprises one or more repeats of the 17 mer to which GAL4 binds (Giniger et al, 1985 Cell 40, 767–774).

As an alternative method of introducing the GAL4 binding domain/transcriptional activator sequence into a plant host cell genome, the construct may comprise Ds ("dissociation") elements, which may then be moved about the genome by the action of a transiently-expressed Ac (Activator) enzyme (e.g. Cocherel et al, 1996 Plant Mol. Biol. 30, 539–551).

In a further aspect, the invention provides a plant or part thereof (e.g. a plant host cell or cell line) comprising the construct defined above. Typically the construct will have become integrated into a plant cell genome and be stably maintained therein. In particular the invention provides a plurality of plants or parts thereof (such as isolated plant cells, or cell lines, or tissue cultures) comprising a library, each plant or part thereof comprising a stably maintained nucleic acid sequence encoding an effective portion of the GAL4 DNA-binding domain as defined above. Conveniently the nucleic acid sequence will be incorporated into the genome of plant cells present in the library.

The library of plants or parts thereof thus provides a very useful resource. The library may be e.g. *Arabidopsis thaliana*, or of any other plant which is routinely used in research. Each plant or part thereof in the library may have a particular pattern of expression of the integrated reporter gene (see, for example, Sundaresan et al., 1995 Genes & Dev. 9, 1797–1810; Klimyuk et al., 1995 Molec. Gen. Genet. 249, 357–365). Thus, introduction of a further gene, having a GAL4-responsive UAS into the cell line, will result in expression of the introduced gene in the same temporal/spatial pattern as the reporter gene, such that researchers can express a particular gene of interest in selected tissues and/or at selected times in a predictable manner.

The invention thus provides a method of expressing a gene of interest in a known (predictable) pattern in a plant or part thereof, the method comprising: introducing the gene of interest into the plant or part thereof, said gene of interest having a GAL4-responsive upstream activation sequence (UAS), characterised in that said plant or part thereof comprises a reporter gene expressed in a known pattern under the influence of a transcriptional activator comprising an effective portion of a GAL4 DNA-binding domain encoded by a sequence in accordance with the invention defined above, such that binding of the transcriptional activator to the UAS causes transcriptional activation of the gene of interest.

The temporal/spatial pattern of expression of the introduced gene or genes of interest will then mirror that already known for the reporter gene. Typically the plant or part thereof will be *Arabidopsis thaliana*, but may be any other plant which is routinely studied (e.g. maize, rice, potato etc).

Typically the gene or genes of interest will be introduced by crossing GAL4-expressing plant cell lines with a plant cell line comprising the gene(s) of interest linked to a GAL4-responsive UAS.

The nucleic acid sequence of the invention has other useful applications, in addition to use as an "enhancer trap", or to direct the expression of a gene or genes of interest in a predictable manner. The modified GAL4 DNA-binding domain/transcriptional activator may also be used to co-ordinate the expression of a plurality of genes of interest. In many circumstances it is desirable to express simultaneously a number of genes in a plant either for research purposes, or for agricultural/industrial motives (e.g. to study metabolic pathways, or to manipulate the synthesis of desirable products such as plant dyes or lipids).

Thus, the invention provides a method for coordinating the expression of a plurality of genes of interest in a plant or part thereof, each of the genes of interest being functionally associated with a GAL4-responsive UAS, characterised in that the plant or part thereof comprises a sequence in accordance with the first aspect of the invention defined above and is capable of expressing a transcriptional activator comprising an effective portion of a GAL4 DNA-binding domain, such that binding of the transcriptional activator to the UAS causes simultaneous transcriptional activation of all of the genes of interest.

Conveniently the plurality of genes of interest may all be associated, in a polycistronic arrangement, with a single UAS, which facilitates their introduction into the plant or part thereof (the genes of interest typically being genes which are not naturally found in the plant or part thereof e.g. mammalian or bacterial genes, or genes from a different plant or possibly natural plant genes which have been the subject of various modifications). Alternatively one or more genes may be operably linked to a respective UAS. The transcriptional activator may be encoded by a sequence already present in the plant or part thereof, or may be introduced simultaneously with (or subsequent to) introduction of the plurality of genes of interest.

The invention will now be further described by way of illustrative examples and with reference to the accompanying drawings, of which:

BRIEF DESCRIPTION OF THE FIGURES

FIG. 1 shows a nucleotide sequence in accordance with the invention encoding a modified GAL4 DNA-binding domain, fused in frame to a sequence encoding a modified transcriptional activation domain from HSV VP16, the vertical line denotes the end of the GAL4 DNA-binding domain;

FIG. 3 shows the nucleotide sequence of part of the nucleic acid construct represented schematically in FIG. 2.

EXAMPLES

Figure 2:
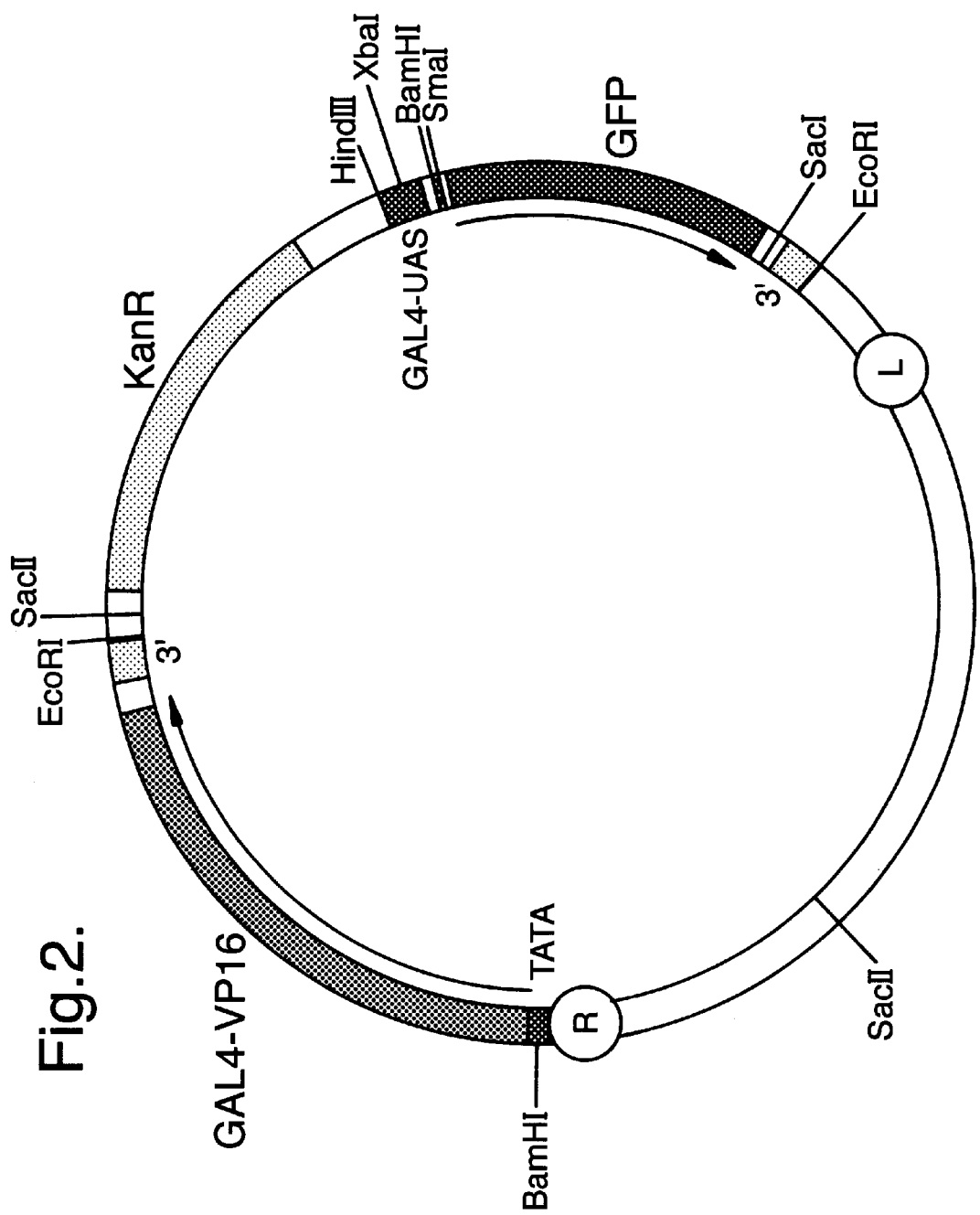
FIG. 2 is a schematic representation of a nucleic acid construct comprising a sequence in accordance with the invention.

The inventors have used an approach similar to that described by Brand & Perrimon (1993, cited above), but adapted it for use in Arabidopsis, using *Agrobacterium tumefasciens*—mediated transformation to produce "enhancer trap" plant cell lines with a transcription activator comprising the GAL4 DNA-binding domain, fused to the activation domain of HSV VP16 (mGAL4-VP16).

Example 1

Construction of mGAL4-VP16 gene

Eight oligonucleotides, which correspond to the modified sequence of the GAL4 DNA binding region, were synthesised.

GAL-5' (28-mer)

GGC AAC AAT GAA GCT ACT GTC TTC TAT C(Seq. ID No.3)

VP16-3' (31-mer)

GGC AGA TCT ACC CAC CGT ACT CGT CAA TTC C     (Seq. ID No.4)

MGAL1 (109-mer)

GGC AAG CTT GGA TCC AAC AAT GAA GCT CCT GTC CTC CAT CGA GCA

GGC CTG CGA CAT CTG CCG CCT CAA GAA GCT CAA GTG CTC CAA GGA

GAA GCC GAA GTG CGC CAA G     (Seq. ID No. 5)

MGAL2 (108-mer)

TCC TCT CGA GGG AAG ATC AGG AGG AAG AGC TGC TCC AGG CGC TCC

AGG CGG GAC TCC ACT TCG GTG AGG TGG GCG CGG GTC AGC GGG GAG

CGC TTG GTT TTG GGA GAG     (Seq. ID No. 6)

MGAL3 (81-mer)

TTC CCT CGA GAG GAC CTC GAC ATG ATC CTG AAA ATG GAC TCC CTC

CAG GAC ATC AAA GCC CTG CTC ACC GGC CTC TTC GTC     (Seq. ID No. 7)

MGAL4 (89-mer)

GGG TGA GGG GCA TGT CGG TCT CCA CGG AGG CCA GGC GGT CGG TGA

CGG CGT CTT TGT TCA CGT TGT CCT GGA CGA AGA GGC CGG TGA GC     (Seq. ID No. 8)

MGAL5 (80-mer)

GGA GAC CGA CAT GCC CCT CAC CCT GCG CCA GCA CCG CAT CAG CGC

GAC CTC CTC CTC GGA GGA GAG CAG CAA CAA GGG CC     (Seq. ID No. 9)

MGAL6 (83-mer)

AGT GGA GCT CGT CCC CCA GGC TGA CGT CGG TCG GGG GGG CCG TCG

AGA CGG TCA ACT GGC GCT GGC CCT TGT TGC TGC TCT CC     (Seq. ID No. 10)

The full-length oligonucleotides were purified by electrophoresis in a 5% polyacrylamide gel containing 7M urea and 90 mM Tris-borate 1 mM EDTA pH8.3 (TBE) buffer. The fractionated oligonucleotides were detected by brief staining with filtered 0.05% toluidine blue dye, excised and eluted overnight at 37° C. in 0.5M ammonium acetate, 0.1% SDS and 0.1 mM EDTA. The eluted DNAs were precipitated and washed with ethanol, and phophorylated using T4 plynucleotide kinase. DNAs (0.5 ug each) were separately resuspended in 50 mM Tris-HCl pH 9.0, 10 mM MgCl$_2$, 10 mM DTT with 1 mM ATP and 5 units T4 polynucleotide kinase, and incubated for 30 mins at 37° C.

The plasmid pCMVGal65 (Cousens et al, 1989 EMBO J. 8, 2337–2342) was used as a source of the GAL4-VP16 sequence with unmodified codon usage. Two restriction endonuclease fragments were isolated from the plasmid. A SacI-SacI fragment, which contains the sequence encoding the DNA binding element of the *Saccharomyces cerevisiae* GAL4 protein, and a SacI-KpnI fragment, which encodes the activation domain of the herpes simplex virus VP16 protein, were purified by fractionation and elution from a low gelling temperature (LGT) 1% agarose gel.

The 5' portion of the mGAL4-VP16 sequence was amplified by the polymerase chain reaction (PCR), using the GAL-5' and MGAL2 oligos as primers and the SacI-SacI GAL4 DNA fragment as a template. Primers and template were incubated under standard conditions with VENT DNA polymerase (New England Biolabs) and subjected to 30 cycles of 94° C. for 30 secs, 50° C. for 1 min, 72° C. for 1 min. The product was cut with XhoI restriction endonuclease and purified after electrophoresis through a 1.5% LGT agarose gel.

The MGAL4 and MGAL5 oligonucleotides were annealed by heating to 65° C. and slow cooling to room temperature. The MGAL3 and MGAL6 oligonucleotides were then added and also annealed to the mixture. The oligonucleotides were then incubated with Klenow fragment of DNA polymerase 1 and T4 DNA ligase in 50 mM Tris-HCl pH 7.5, 10 mM MgCl$_2$, 10 mM DTT, 1 mM dNTPs and 1 mM ATP for 60 mins at 37° C. An excess of MGAL3 and MGAL6 oligonuceotides were added, and the mixture was subject to PCR amplification, as above. The product was cut with the restriction endonucleases XhoI and SacI, and purified after electrophoresis through a 1.5% LGT agarose gel.

The three gel-purified restriction fragments: (1) the GAL-5'/MGAL2 PCR-amplified product, corresponding to the 5' portion of the GAL4 DNA binding domain, (2) the MGAL3-6 annealed and amplified product, corresponding to the 3' portion of the GAL4 DNA binding domain, and (3) the SacI-KpnI fragment from pCMVGal65, corresponding to the VP16 activation domain; were mixed and ligated with T4 DNA ligase in 50 mM Tris-HCl pH 7.5, 10 mM MgCl$_2$, 10 mM DTT and 1 mM ATP at 20° C. overnight. The ligated product was PCR amplified (as above) using MGAL1 and VP16-3' as primers. The product, containing the entire modified GAL4-VP16 sequence was cut with BamHI and ligated to PBI121 (Jefferson et al, EMBO J. 6:3907, 1987) which had been cut with SacI, blunt ended by treatment with T4 DNA polymerase, and re-cut with BamHI. The recombinant plasmid (pBIN 35S-mGAL4-VP16) contained the mGAL4-VP16 gene downsteam of the constitutive 35S plant promoter.

In FIG. 1, the lower DNA sequence is that of the fusion gene (Seq. ID No. 1), encoding in the 5' portion the GAL4 DNA-binding domain, and encoding in the 3' portion the transcriptional activation domain from HSV VP16. The wild-type sequence is shown above for comparison. It will be seen that the wild type GAL4 DNA-binding domain coding sequence is A/T rich (A/T % content is shown on the right for each line of sequence), and it is believed that this causes inefficient expression in plants. In particular, it is believed that the A/T rich DNA comprises one or more regions which, when transcribed, are recognized as mRNA splice sites in plant cells. The altered nucleotides are shown outlined in FIG. 1. The encoded polypeptide sequence is shown below (Seq. ID No. 2). The modifications to the nucleotide sequence were carefully selected to ensure that there was no resulting change in the encoded amino acid sequence. The numbers above the sequences represent the number of the nucleotide or amino acid at that position. Certain restriction endonuclease sites are also shown.

The 35S promoter and mGAL4-VP16 gene were excised by digestion with the restriction endonucleases HinDIII and EcoRI, purified by 1% LGT agarose gel electrophesis, and subcloned into a vector containing a GAL4-responsive mgfp5-ER marker gene (see Example 2 below). The resulting construct is shown in FIG. 2, in which R and L represent right and left Ti plasmid border sequence. The GAL4-VP16 fusion gene is downstream of the TATA-box region (nucleotides −48 to +1) of the CaMV 35S gene, were inserted adjacent to the right Ti border. The plasmid also contains the kanamycin resistance (Kan R) selectable marker, and a reporter gene (GUS or GFP) operably linked to a synthetic GAL4-UAS promoter sequence. Certain restriction endonuclease sites are also shown.

FIG. 3 shows the nucleotide sequence (Seq. ID No. 15) of the plasmid across the junctions of the Ti right border, the CaMV35S TATA box, and the start of the GAL4 DNA-binding domain coding region.

The mGAL4-VP 16 gene was directly assayed for activity in transformed Arabidopsis plants by Agrobacterium-mediated transformation (Valvekens et al Proc. Natl. Acad. Sci. USA 85:5536–5540, 1988).

Example 2

Construction of GAL-GFP Enhancer Trap Vector
Modification of the T-DNA Right Border.

The plasmid pBIN19 (Bevan, M. Nuc. Acids Res. 12:8711–8721, 1984) was digested with the restriction endonuclease SacII, and a 2.6 Kb fragment containing the Agrobacterium T-DNA right border sequence was subcloned into SacII cut pGEM 5Zf(Genbank accession No. X65308; commercially available from Promega). The bacteria containing the recombinant phagemid were superinfected with helper phage to produce single strand phagemid DNA.

A synthetic mutagenic oligonucleotide ("TR+": ATA TCC TGT CAA ACA CTG GAT CCG AGC TCC AAT TCA TAG TTT AAA CTG AAG GCG GG; Seq. ID No. 11) was kinased and annealed to the purified phagemid DNA, extended on the template using T7 DNA polymerase, and ligated using T4 DNA ligase. The DNA was transformed into bacteria, and recombinant plasmids (pTr+) were screened for the insertion of new sites for the restriction endonucleases BamHI, SmaI and EcoRI immediately adjacent to the T-DNA right border.

Insertion of TATA Box Region.

The TATA box region of the 35S promoter was PCR amplified from pBI121 using oligonucleotides complementary to the −48 region of the promoter (oligonucleotide Δ35SBglII; GGC AGA TCT TCG CAA GAC CCT TCC TCT ATA TAA GG; Seq. ID No. 12) and the downstream β-glucuronidase gene (oligonucleotide GUSSnaBI; CAC ACA AAC GGT GAT ACG TA; Seq. ID No. 13). The PCR product was cut with restriction endonucleases BglII and BamHI and ligated to BamHI cut pTr+. The resulting recombinant plasmid (pTr+Δ35S) contained a minimal (naive) promoter positioned adjacent to the T-DNA right border.

Insertion of 35S Promoter Driven mGAL4-VP 16 Gene.

Derivatives of the GAL4 with unmodified codon usage were inserted into the pTr+Δ35S plasmid in unsuccessful trial experiments, and one of these constructions (the insertion of a truncated GAL4 gene derived from pMA236; Ma et al, 1988 Nature 334, 631–633) had resulted in the insertion of a unique HindIII site immediately adjacent to the BamHI site in pTR+Δ35S. This plasmid, pTr+ΔGAL4, was digested with restriction endonucleases HindIII and EcoRI, and ligated with the HinDIII-EcoRI fragment from pBIN 35S-mGAL4-VP 16, to introduce the 35S-driven mGAL4-VP 16 gene. The Agrobacterium sequences from this plasmid (pTr+35S-mGAL4-VP 16) were then recloned into a binary plant transformation vector which contained a GAL4-responsive marker gene (see below), for testing in planta.

Construction of a Synthetic GAL4-Responsive Promoter.

A HinDIII-XbaI restriction endonuclease fragment containing five optimised binding sites for GAL4 was excised from the plasmid pUAST (Brand & Perrimon, 1993 Development, 118, 401–415), and ligated into HinDIII-XbaI cut pBI101 (Jefeerson et al., 1987 EMBO J. 6, 3901–3907) upstream of the GUS gene (to make pBINΔUAS-GUS). A sequence corresponding to the −90 region of the 35S promoter was PCR amplified using oligonucleotides DELAS1 (GAA CTC TAG AAG CTA CTC CAC GTC CAT AAG GGA CAC ATC ACA ATC CCA CTA TCC TTC GC; Seq. ID No. 14) and GUSSnaBI (see above). The product was XbaI-BamHI cut and cloned into similarly cut pBIN ΔUAS-GUS. The resulting plasmid (pBIN UAS(-90-AS1)GUS) contains a synthetic GAL4 promoter upsteam of the β-glucuronidase (GUS) coding sequence. The GUS gene was then replaced with that of the green fluorescent protein (GFP).

GAL4-Responsive mgfp5-ER Gene.

We have extensively mutated the green fluorescent protein gene for optimised expression in plants. The optimised gene is called mgfp5-ER (Siemering et al, Current Biology 6:1653–1663, 1996; WO96/27675).

The mgfp5-ER gene has been cloned into the plant transformation vector pBI121, and we have excised a BamHI-SacI fragment, which contains the coding sequence, and have inserted this into BamHI-SacI cut pBIN UAS(-90-AS1)GUS to replace the GUS gene. This plasmid (pBIN UAS(-90-AS1)mgfp5-ER) was cut with SacII, and ligated with the SacII fragment containing the modified T-DNA right border and mGAL4-VP16 gene from pTr+35S-mGAL4-VP16, to give pBIN 35S-GAL4-VP16+UAS-mgfp5-ER (abbreviated to pBIN35S-GAL-GFP).

Testing of the pBIN35S-GAL-GFP Vector.

The pBIN 35S-GAL-GFP plasmid was introduced into *Agrobacterium tumefaciens* strain LBA4044 (Jefferson et al., EMBO J. 6:3901–3907, 1987) by electroporation, followed by selection on kanamycin-containing plates. The Agrobacterium strain was used to transform Arabidopsis using the technique described below. Plants were scored for the GAL4-dependent induction of GFP fluorescence after transformation.

Construction of GAL-GFP Enhancer Trap Vector

The pTR+35S-mGAL4-VP16 plasmid was treated with BamHI (to excise the 35S promoter sequences) and religated using T4 DNA ligase. This plasmid (pTR+mGAL4-VP16) contains the modified GAL4-VP16 positioned with a minimal promoter adjacent to the T-DNA right border. The T-DNA sequences were then excised by digestion with SacII, and ligated with similarly cut pBIN UAS(-90-AS1) mgfp5-ER. This produced pBIN GAL-GFP, which contains the highly active mGAL4-VP16 transcription activator, responsive to adjacent enhancer elements, and a GAL4-dependent GFP gene. GFP fluorescence is produced in response to GAL4-VP16 activation.

Enhancer Trap Screen.

The enhancer trap vector pBIN GAL-GFP was introduced into *Agrobacterium tumefaciens* (see details below) LBA4044, and has been used to generate over 7,500 transformed Arabidopsis seedlings. Transgenic seedlings have been screened directly for GAL4-mediated GFP expression, and seeds were collected from expressing plants. We have a library of over 250 Arabidopsis lines which show stable inheritable patterns of GAL4 -mediated GFP expression in the root.

Transactivation.

To demonstrate GAL4-mediated transactivation of a foreign gene we have generated transgenic Arabidopsis that contain the T-DNA sequences from pBIN UAS(-90-AS1) GUS). In the absence of GAL4-VP16, these plants do not express the GUS gene. However, when genetically crossed with lines expressing the mGAL4-VP16 gene, the GUS gene is activated in a pattern of expression which accurately reflects that of the mGAL4-VP16 gene from the donor parent (see Example 3 below).

Example 3

Figure 4A:
FIGS. 4a–4d show micrographs of roots of plants comprising a sequence in accordance with the invention.
Figure 4C:
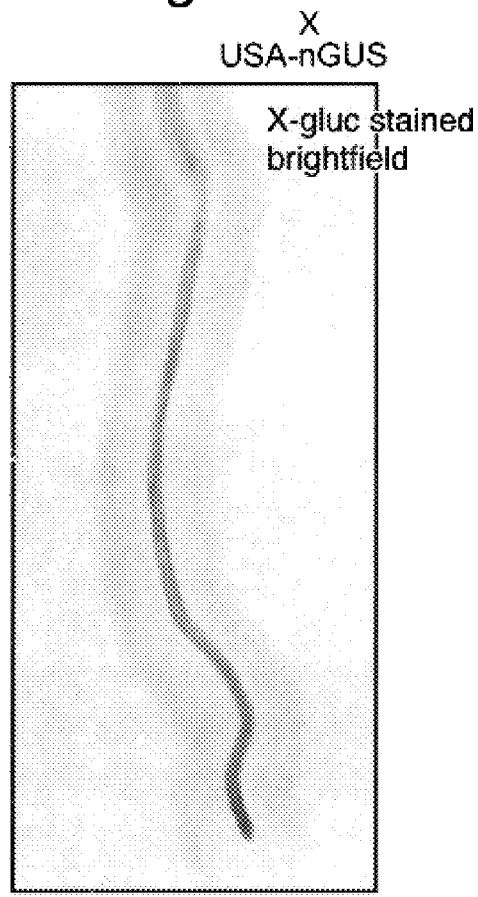
Figure 4B:
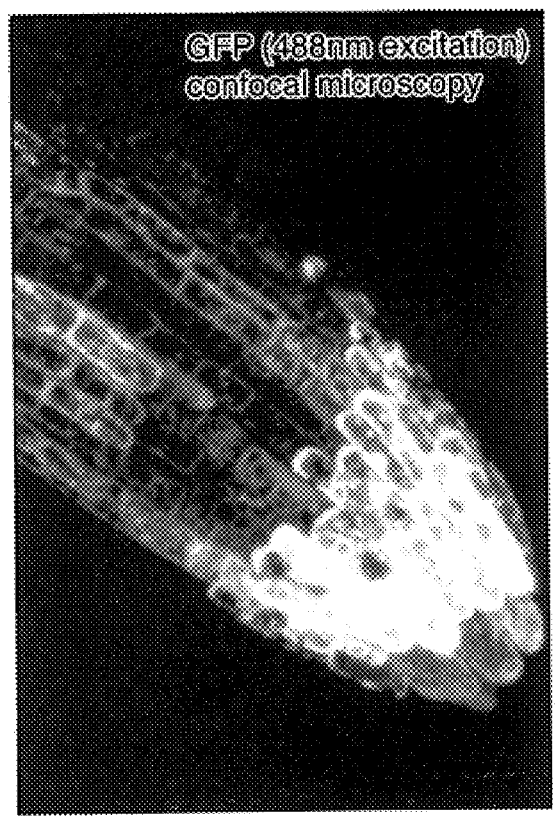

A stable transformed line (J2302) of *Arabidopsis thaliana*, which formed part of the library described above, expressed modified GFP (under the influence of the mGAL4-VP16 activator) in the cells of the extreme root tip (see FIGS. 4a and 4b).

FIG. 4a is a low power micrograph showing GFP-mediated epifluorescence (400 nm excitation) at the root tip. FIG. 4b is a higher magnification confocal micrograph (488 nm excitation) showing the area of GFP-mediated fluorescence in greater detail.

Figure 4D:
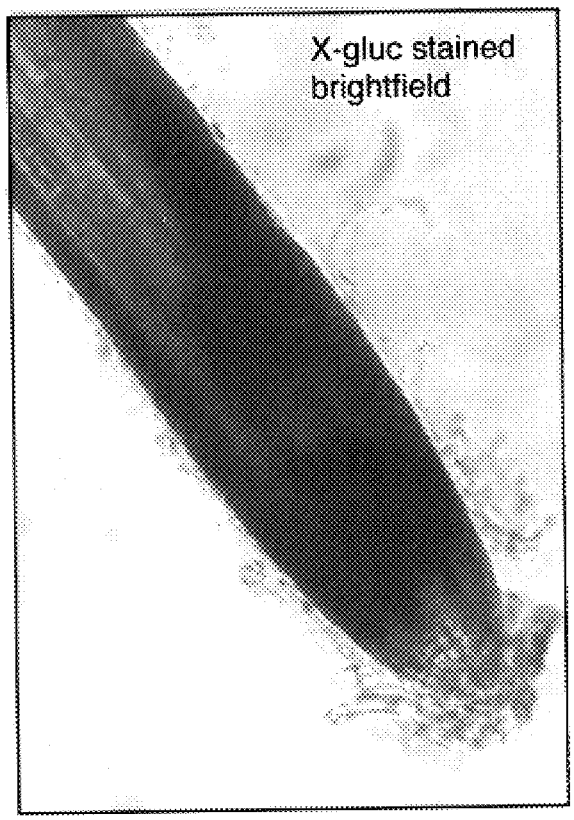

The line J2302 was crossed (using standard techniques) with another Arabidopsis line which comprised a stable, silently-maintained GUS reporter gene operably linked to a GAL4-responsive UAS. The product of the cross, as expected, proceeded to express GUS, under the influence of the GAL4-VP16 transcriptional activator, in the same pattern as the GFP reporter gene in J2302 (i.e. at the extreme root tip). Suitably stained samples, imaged by brightfield microscopy, are shown in FIGS. 4c and 4d, and demonstrate GUS reporter gene activity (darkest staining) at the root tip.

This illustrates that the modified GAL4 DNA-binding domain sequence can (i) successfully be used in the construction of enhancer trap vectors;

(ii) express genes of interest (as exemplified by GUS) in a predictable pattern; and (iii) co-ordinate the simultaneous expression of a plurality of genes of interest (as exemplified by GFP and GUS).

Example 4

Transformation of *Arabidopsis thaliana*

The methods employed are based on those originally disclosed by Valvekens et al. 1988. Proc,. Natl. Acad Sci. 85, 5536–5540).

Media

Unless otherwise stated all procedures were carried out aseptically using sterile solutions and equipment. All media are used in standard plastic disposable petri dishes or, for later stages, Magenta GA 7 pots (Magenta Corp., USA). Hormones are dissolved in dimethyl sulfoxide (DMSO) as ×1000 stocks. Hormones and antibiotics are added after autoclaving and cooling of the media to 65° C.

1. Germination medium (GM) comprised: 1× Murashige and Skoog salt mixture; 1% sucrose; 100 mg/l inositol; 1.0 mg/l thiamine; 0.5 mg/l pyridoxine; 0.5 mg/l nicotinic acid; 0.5 g/l 2-(N-morpholino)ethanesulfonic acid (MES); (adjust to pH 5.7 with 1M KOH); and 0.8% Difco Bacto agar (for solid GM medium).

1a. GM K50

As GM, but supplemented with: 50 mg/l kanamycin (Sigma)

2. Callus-inducing medium (CIM) comprised: 1× Gamborg's B5 medium; 2% glucose; 0.5 g/l MES (pH 5.7, adjusted with 1N KOH); 0.5 mg/l 2,4-D (Sigma); 0.05 mg/l kinetin (Sigma); and 0.8% agar (for solid CIM medium).

3. Shoot-inducing medium with Vancomycin (SIM V750 K50) comprised: Gamborg's B5 medium; 2% glucose; 0.5 g/l MES (pH 5.7); 0.8% agar; 5 mg/l N6-(2-isopentenyl) adenine (2 ip); 0.15 mg/l indole-3-acetic acid (IAA); 750 mg/l vancomycin; and 50 mg/l kanamycin.

3a. SIM V500 K50

As SIM, but supplemented with: 500 mg/l vancomycin; and 50 mg/l kanamycin.

4. Root-inducing medium (RIM) comprised: Gamborg's B5 medium; 2% glucose; 0.5 g/l MES (pH 5.7); 0.8% agar; 12.5 mg/l indole butyric acid (IBA); and 50 mg/l cefotaxime.

Growth of Plants (i) Place seeds into a 15 ml polypropylene centrifuge tube.

(ii) Add ethanol for 2 min. Remove ethanol with pipette.

(iii) Replace with 5% commercial bleach (~0.25% available chlorine) containing one drop of NP40 per 50 ml. Leave for 15 min, shaking regularly.

(iv) Wash seeds in sterile, distilled water for at least three times.

(v) After last wash, add the sterile seeds to 100 ml of GM in a conical flask. Grow with shaking for 2–4 weeks in a culture room at 20–25° C.

Agrobacterium-Mediated Transformation

1. Day One (i) Using a scalpel, cut-off all the green (upper) parts of the plantlets to leave only the root systems.

(ii) Lay out the roots on plates containing solid CIM. Gently press down on each bunch of roots to ensure that they are in contact with the surface of the agar.

(iii) Incubate for 3 d in growth room (22° C., continual light).

2. Day Four (i) After ensuring that there is no visible sign of contamination, collect the callus-induced roots in an empty petri dish.

(ii) Cut the roots into 0.5 cm explants.

(iii) Add 3–5 ml of Agrobacterium culture which has been grown overnight at 28° C. in Luria broth, and washed by centrifugation. Swirl with blunt-nosed forceps. Leave to co-cultivate for 2 min.

(iv) Blot the roots dry on double-thick sterile filter-paper (Whatman No. 1) in a petri dish.

(v) Place the explants onto solidified CIM medium in a petri dish. and gently press them onto the surface to ensure contact with the medium.

(vi) Incubate plates in the growth room for 2 d to allow co-cultivation of Agrobacterium.

3. Day Six (i) Transfer the explants to a petri dish in 20–25 ml of water. Agitate with blunt-nosed forceps to wash off the agrobacteria. The bathing medium should become somewhat turbid. Transfer the root pieces to a sieve and repeat the washing. Then lift the sieve out of buffer and drain. Press down the explants down onto the mesh to remove as much buffer and agrobacteria as possible. Push the semi-dried explants together into a mass.

(Custom-made, autoclavable and re-usable, sieves are used to hold the explants during Agrobacterium infections and washings of root explants. These sieves are made from 100 ml plastic three-cornered beakers and 100 um nylon mesh. The top 3–4 cm is cut off the beaker and the mesh held in place across the bottom of this piece by pushing a ring 2 cm high cut from just above the base of the beaker into the lower portion of the top part. The two pieces are sealed together by pushing a hot metal rod through them in several places.)

(ii) Blot small bundles of root material on double-thick sterile filter-paper in a petri dish until dry and transfer to solidified SIM V750 K50 medium, taking care that root explants are in close contact with the medium.

(iii) Incubate in growth room.

Regeneration (i) In growth room, tiny green kanamycin resistant calli appear on the yellowish root-explants after 3 weeks.

(ii) Every 2 weeks, transfer explants to fresh SIM V750 K50. Shoots (often initially vitreous) intermittently appear from the green calli over the next several weeks.

(iii) Transfer these shoots to RIM, where roots will develop over a period of 2 to 3 weeks (iv) After the formation of roots, transfer the plantlets to GM in vented Magenta GA7 pots or directly to soil. Ensure that the humidity is kept low to ensure good seed set.

(v) Harvest seed pods when they turn yellowish-brown and are therefore mature.

Germination and Screening of F1 Progeny

To test for transformation, F1 seedlings are germinated on GM K50.

(i) Put seeds on GM K50 (surface sterilise the seeds if necessary).

(ii) Put petri dishes in the dark at 4° C. (refrigerator) for 3–5 d, to break seed dormancy.

This is not necessary if seeds were stored for more than a month.

(iii) Incubate petri dishes in growth room for 2 weeks. Sensitive seedlings form neither roots nor leaves, and have white cotyledons. Transformed seedlings are phenotypically normal.

(iv) Transgenic callus and shoots were screened for GFP expression using a inverted fluorescence microscope (Leitz DM-IL) fitted with a filter set (Leitz-D excitation BP355-425, dichroic 455, emission LP460 ) suitable for the main 395 nm excitation and 509 nm emission peaks of GFP. The use of a 7 mm threaded extension tube with a 4× objective (EF 4/0.12) gave a greater working distance, and has allowed the convenient direct observation of tissue within inverted sealed petri dishes. A 100 Watt long wavelength hand-held UV lamp (UV Products, B100AP) was also used for routine monitoring of transgenic shoots and plants. Transgenic Arabidopsis F1 seedlings were grown in sterile agar culture for 5 days, and were mounted in water under glass coverslips for microscopy. The specimens were examined using a BioRad MRC-600 laser-scanning confocal microscope equipped with a krypton-argon laser and filter sets suitable for the detection of fluorescein and texas red dyes (BioRad K1/K2), and a Nikon 60× PlanApo N.A. 1.2 water immersion objective.

What is claimed is:

1. A nucleic acid sequence, which is set forth in SEQ ID NO:1.

2. A sequence according to claim 1, further comprising a structural and/or regulatory sequence in operable linkage to the sequence encoding the effective portion of the GAL4 DNA-binding domain.

3. A sequence according to claim 1, wherein the nucleic acid encodes a peptide or polypeptide, having transcriptional activation activity, in operable linkage with the sequence encoding the effective portion of the GAL4 DNA-binding domain.

4. A sequence according to claim 1, wherein the sequence encodes a peptide or polypeptide, having transcriptional activation activity in a plant cell, which is a modified portion of GAL4, VP16, GCN4 or a designed sequence which does not naturally occur.

5. A nucleic acid construct comprising a sequence in accordance with claim 1.

6. A construct according to claim 5, capable of inserting a nucleic acid sequence which is set forth in SEQ ID NO:1 into the genome of a plant host cell.

7. A construct according to claim 5, further comprising a reporter gene in operable linkage with a GAL4-responsive upstream activation sequence (UAS).

8. A construct according to claim 5, comprising a sequence encoding GUS or green fluorescent protein (GFP) suitable for expression in a plant cell.

9. A construct according to claim 5, comprising T-DNA borders or Ds elements.

10. A nucleic acid construct comprising a sequence according to claim 1 wherein expression of said sequence is under the control of an enhancer-dependent plant promoter.

11. A construct according to claim 5, further comprising a selectable marker gene.

12. A plant or part thereof comprising a nucleic acid sequence according to claim 1.

13. A plant or part thereof transformed with a construct according to claim 5.

14. A plant or part thereof according to claim 13, wherein the sequence is stably integrated in the plant genome.

15. A library comprising a plurality of plants or parts thereof, each plant or part thereof comprising a stably integrated nucleic acid sequence according to claim 3, which sequence causes the expression of a reporter gene in a known temporal and/or spatial pattern.

16. A library according to claim 15, made by the introduction of a nucleic acid construct comprising a sequence which is set forth in SEQ ID NO:1 into a plurality of plants or parts thereof.

17. A library according to clam 15, comprising a plurality of *Arabidopsis thaliana* plants.

18. A method of expressing a gene of interest in a known pattern in a plant or part thereof, the method comprising: introducing the gene of interest into the plant or part thereof, said gene of interest having a GAL4-responsive upstream activation sequence (UAS), wherein said plant or part thereof comprises a reporter gene expressed in a known pattern under the influence of a transcriptional activator comprising a GAL4 DNA-binding domain activity encoded by a sequence according to claim 1, such that binding of the transcriptional activator to the UAS causes transcriptional activation of the gene of interest.

19. A method according to claim 18, wherein the gene of interest is introduced into one or more plants or parts thereof from a library comprising a plurality of plants or parts thereof, each plant or part thereof comprising a stably integrated nucleic acid sequence which is set forth in SEQ ID NO:1 which sequence causes the expression of a reporter gene in a known temporal and/or spatial pattern, said library being made by the introduction of a nucleic acid construct comprising a nucleic acid sequence which is set forth in SEQ ID NO:1 into a plurality of plants or parts thereof.

20. A method for coordinating the expression of a plurality of genes of interest in a plant or part thereof, each of the genes of interest being functionally associated with a GAL4-responsive UAS, wherein the plant or part thereof comprises a sequence according to claim 1 and is capable of expressing a transcriptional activator comprising an effective portion of a GAL4 DNA-binding domain, such that binding of the transcriptional activator to the UAS causes simultaneous transcriptional activation of all of the genes of interest.

21. A method according to claim 20, wherein at least some of the genes of interest are arranged polycistronically and associated with a single GAL4-responsive UAS.

22. A method according to claim 20, wherein genes of interest are functionally associated with respective GAL4-responsive UASs.

* * * * *